United States Patent
Zhang

(10) Patent No.: US 10,295,544 B2
(45) Date of Patent: May 21, 2019

(54) APPARATUS AND METHOD FOR HIGH TRHOUGHPUT IMMUNOBLOTING

(71) Applicant: YANTAI ZESTERN BIOTECHNIQUE CO. LTD., Yantai, Shandong (CN)

(72) Inventor: Jiandi Zhang, Fairfax, VA (US)

(73) Assignee: QUANTICISION DIAGNOSTICS INC., Chapel Hill, NC (US)

(*) Notice: Subject to any disclaimer, the term of this patent is extended or adjusted under 35 U.S.C. 154(b) by 239 days.

(21) Appl. No.: 15/433,586

(22) Filed: Feb. 15, 2017

(65) Prior Publication Data

US 2018/0231538 A1 Aug. 16, 2018

(51) Int. Cl.
*G01N 33/68* (2006.01)
(52) U.S. Cl.
CPC ................ *G01N 33/6803* (2013.01)
(58) Field of Classification Search
None
See application file for complete search history.

(56) References Cited

U.S. PATENT DOCUMENTS

2015/0011437 A1* 1/2015 Zhang ............... B01L 3/5085
506/39

OTHER PUBLICATIONS

ELISA Protocol (published Feb. 2016). (Year: 2016).*
Mahmoudifard et al. Materials Science and Engineering 2016 58: 586-594 (Year: 2016).*
Mazet, F et al. "A high-density immunoblotting methodology for quantification of total protein levels and phosphorylation modifications", Scientific Reports, Nov. 23, 2015, vol. 5.

* cited by examiner

*Primary Examiner* — Changhwa J Cheu
(74) *Attorney, Agent, or Firm* — Novick, Kim & Lee, PLLC; Allen Xue

(57) ABSTRACT

This disclosure provides high throughput immunoblot methods and apparatus for an antigen such as a chemical compound, a peptide, a nucleic acid, or a protein released from cells or virus particles in situ. The method yields highly sensitive and accurate results and is useful in analyze complex system including an antigen from cell or tissue lysate.

19 Claims, 8 Drawing Sheets

APPARATUS AND METHOD FOR HIGH TRHOUGHPUT IMMUNOBLOTING

FIELD OF THE DISCLOSURE

The present disclosure relates to methods and apparatus for high throughput immunobloting for an antigen. In particular, this disclosure provides methods and apparatus for performing immunoblot in a multi-unit plate format with improved speed and accuracy.

BACKGROUND

Protein analysis is the basis of modern biological research. It centers on antigen-antibody interaction to measure levels of antigen of interest under various medical or experimental conditions. An antigen by definition is a foreign molecule that triggers the production of an antibody by the immune system when introduced into the body. The high specificity of the antibody against a specific antigen makes it a powerful tool in clinical, pharmaceutical and biomedical research.

An antigen includes, but not limited to a chemical compound, a peptide, a protein, an RNA, a DNA, a cell (proteins released in situ), or a virus particle (proteins released in situ). The molecule of antigen, as a whole or in part, may be introduced into a host animal, such as a donkey, a goat, or a rabbit to generate a large quantity of antibody against the introduced antigen of interest. Furthermore, the introduced antigen, or part of the antigen, may have more than one epitopes, thus may generate a corresponding number of antibodies against the antigen of interest.

A typical immunodetection process has three major steps. The first step is sample application, in which prepared samples containing an antigen of interest are first bound to a surface, such as nitrocellulose or PVDF membrane or other solid phase like multi-well plate with protein binding capacity. The second step is to form and label the antigen-antibody complex (i.e., immunocomplex) of interest. This step involves the sub-steps of blocking, incubation and washing. In the blocking sub-step, non-specific protein binding sites on the membrane are blocked using a blocking buffer to shield them from non-specific protein. After blocking, the membrane is incubated in the incubation step with antibody against the antigen of interest to form membrane-bound antigen-antibody complex. The unbound antibodies are washed away. The antibody used herein is often commercially available as a pre-labelled antibody. One may also perform the labeling sub-step on site. In either case, the antibody shall be labelled, either directly with a reporter, e.g., a reporter enzyme, or indirectly labelled using a secondary antibody conjugated with a reporter.

The third step is detection. Signals emitted by the reporter enzyme are detected and recorded, which yield information related to the quantity or quality of the immunocomplex bound on the membrane. In both Dot blot analysis and Western blot analysis, the final result of the immunodetection analysis can be further indirectly quantified through densitometric analysis.

There are numerous variations in each individual step of this procedure. For example, the first step—sample application—has many variations, including direct sample application on a piece of membrane in Dot blot analysis, transferring from gel to a piece of membrane in Western blot analysis, or coating of samples to the wells of a microplate in ELISA analysis. Several more modifications have been made to the second step of forming immunocomplexes, including the various procedures and buffer compositions to minimize direct antibody binding while preserving the formed immunocomplex on the membrane. In most cases, the primary antibody is not directly labeled with a reporter enzyme. A secondary antibody against the primary antibody coupled directly or indirectly with a reporter enzyme would be used to label primary antibodies bound to the antigen of interest on the surface of membrane. The secondary antibody may be further labeled with small molecules like Biotin. For example, a Streptavidin coupled HRP may be used to further enhance the signal.

Different methods of labeling the antibody in turn necessitate different corresponding detection methods. For example, the third step of detection may be a color reaction by visual inspection or chemiluminescence signals detectable through scanner, X-ray film or microplate reader, etc. The antibody may also be fluorescence-labeled and detected through scanner In conventional immunoblot analysis, signals emitted by the labelled immunocomplexes are first acquired as images (e.g., dark bands or dots) through X-ray film or scanner. An image processing equipment (e.g., a densitometer) and/or an image processing software (e.g., ImageJ) is needed to read the image and translates the optical density into a number(s) that indicates the amount of the immunocomplexes.

Among available immunoblotting methods (e.g., dot blot, Elisa, Western blot, reverse phase protein microarray), Western blot probably is the most commonly used in basic lab research. In a Western blot analysis, prepared samples containing the antigen of interest are first separated according to molecular weight through gel electrophoresis, and the separated proteins are transferred through an electroblotting step to either a nitrocellulose membrane or a PVDF membrane.

In an immunodetection process that follows, the levels of the antigen of interest in the prepared samples are detected on the spot in a typical reporter enzyme-based reaction, and quantified indirectly through densitometric analysis. For example, using ImageJ, the bands in the gel image in Western blot analysis are manually selected before calculating numeric values of each band using software. In this process, the specificity of immunodetection is validated by both the antigen-antibody interaction and the expected molecular weight of the antigen of interest, which eliminates false signals commonly observed in Dot blot analysis.

ELISA assay allows direct quantification of signals in a multi-well plate format. However, the protein binding capacity of an Elisa plate is usually of less than 1 $\mu g/cm^2$. In contrast, a typical membrane for traditional immunoblotting, regardless of nitrocellulose or PVDF membrane, has a protein binding capacity of 100 to 200 $\mu g/cm^2$. The low binding capacity of ELISA limits its use in the lab.

In short, new and improved methods for analyzing antigen in a complex assay are needed. Suitable methods should be easy to use, inexpensive, fast in assay development, and should yield results comparable to or better than Western blot analysis in measuring the content of antigen in the lysate.

SUMMARY

The present disclosure provides the method of QDB (Quantitative Dot Blot) analysis that allows for rapid and accurate quantification of an antigen in a sample in a high throughput format. The QDB analysis eliminates the gel electrophoresis step in Western blot analysis. It has better sensitivity and reliability than the existing Dot blot and better flexibility than ELISA assay.

In one embodiment of the QBD method, an antigen is bound to a plurality of membrane units. Each membrane unit is affixed to one of a plurality of supports. A primary antibody that interacts with the antigen is selected. The primary antibody binds to the antigen to form a plurality of immunocomplexes on the membrane.

The immunocomplexes attached to the plurality of membrane units are labeled with a labelling substance. The labelled immunocomplexes emit signals, e.g., photons or radiations. Further, signals emitted by the labelled immunocomplexes are detected using a machine.

In some embodiments, the labelling substance is a reporter enzyme, a radioactive isotope, a DNA reporter, a fluorogentic reporter, an electrochemiluminescent tag, or mixtures thereof, while reporter enzymes can be HRP, AP or glucose oxidase and the fluorogentic reporters can be phycoereythrin. In addition, the labeling substance is conjugated with the primary antibody or conjugated with a secondary antibody attached to the primary antibody.

In still other embodiments, the plurality of supports are parts of a plate to facilitate QDB analysis (hereinafter referred to as the "QDB plate"). The QDB plate has a planar structure with a plurality of supports spaced away from a planar surface of the planar structure. The support can be any structure that holds a piece of membrane while allowing the membrane to be exposed to a solution when the support is immerse in the solution. Accordingly, the support can be a ring with a hollow center portion. The membrane is attached to the ring. Each of the supports can be a post, a section of a wall, etc. Alternatively, the membrane may also be coated or supported on a solid surface.

In further embodiments, each of the support and the associated membrane and linking member(s) constitute a membrane unit so that the QDB plate is also referred to as a multi-unit plate. The QDB plate is insertable into a multi-well plate to form an assembly. In this assembly, the membrane units in the QDB plate are inserted into corresponding wells in the multi-well plate.

In still other embodiments, each well in the multi-well plate may hold a solution, e.g., a buffer solution, so that the membrane in the corresponding membrane unit is exposed to the solution.

Signals emitted by the labelled immunocomplexes may be imaged or not imaged. When the signals are imaged, the images may be captured using a permanent medium (e.g., photographic film). The image on the permanent medium is then processed using a densitometer with an image process software to give readings of the intensity of the signals.

In the embodiments of this disclosure, the signals emitted from each of the membrane units can be read without first being registered as images. For example, the light signals (i.e., photons) from the membrane are received by a microplate reader having a photomultiplier, which directly provides a numerical reading of the amount of the signals received. Since the membrane units are spaced away from each other, signals emitted from different membrane units can be individually acquired. The signal from each membrane unit is directly translated into a numeric value that corresponds to the intensity of the signal emitted by the labelled immunocomplexes attached to that particular membrane unit.

In further embodiments, imaging of the signals and the direct reading of the signals (without imaging) may be carried out simultaneously.

In still an embodiment, this disclosure provides a method for immunoblot analysis, which includes providing a multi-unit plate having a plurality of membrane units spaced away from one another, wherein each membrane unit comprises a membrane; binding an antigen to one or more of the plurality of membrane units; selecting a primary antibody that interacts with the antigen; binding the primary antibody to the antigen to form immunocomplexes affixed to one or more of the plurality of membrane units, wherein the primary antibody is directly conjugated with a reporter enzyme, or indirectly conjugated with a reporter enzyme through one or more secondary antibodies; and detecting, from one or more of membrane units, light signals emitted by the reporter enzyme in the immunocomplexes attached to each of the one or more of membrane units.

DETAILED DESCRIPTION

Unless otherwise defined in this disclosure, all technical and scientific terms used herein have the same meaning as is commonly understood by one of skills in the art to which this disclosure belongs.

Figure 1:
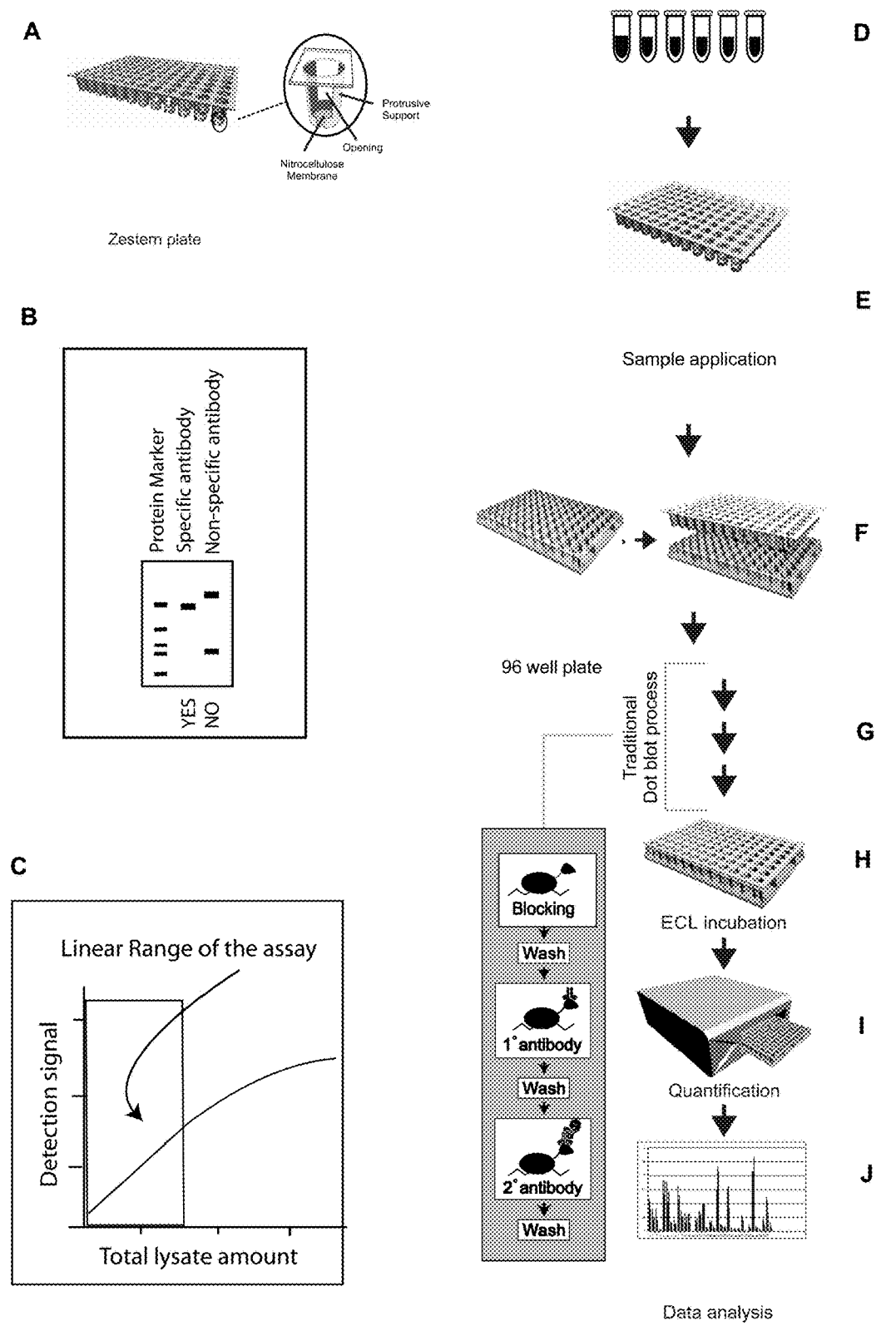
FIG. 1 illustrates an embodiment of a QDB process of this disclosure.

FIG. 1 illustrates steps and devices in a QDB analysis of the current disclosure. The first step in this process is to validate the specificity of the detection antibody. FIG. 1B illustrates validation through Western blot analysis. For a specific antibody, the Western blot analysis should show only one band at the right molecular weight. Any antibody that detects two or more bands in Western blot analysis is not specific. Only specific antibodies are suitable for QDB analysis.

Further, a dose curve is constructed to determine the linear range of the assay. A common practice is to serially dilute a sample and plot a curve showing signal vs. known dosages, i.e., the dose curve (FIG. 1C). The linear range in that curve informs the range of the amount of sample with which the QDB analysis shall be carried out. The same lysate sample may have different linear ranges if tested in different equipment using different methods. It is necessary that the dose curve is constructed using the same equipment and method with which other samples would be studied.

Once a specific antibody has been identified (e.g., FIG. 1B) and the linear range of the dose curve established (e.g., FIG. 1C), a sample of interest (e.g., cell culture, animal studies, tumor research) for immunodetection analysis is prepared and placed in a container (FIG. 1D). The non-limiting examples of the sample may contain a chemical molecule, a peptide molecule, a protein molecule, an RNA molecule, a DNA molecule, a traditional antibody containing two heavy chains and two light chains, a recombinant antibody or fragment thereof, a bacterial cell, a virus particle, a cell, a particle, or a product comprising any two or more of the above connected by crosslinking. The samples are then loaded onto a special multi-unit plate, aka QDB plate (FIG. 1E).

Details of an embodiment of a 96-well QDB plate are shown in FIG. 1A. This embodiment of the QDB plate has a planar surface with a plurality of openings—96 holes in this embodiment. Each opening corresponds to a well extending away from the planar surface. The "bottom" of the well is a piece of nitrocellulose membrane or is a surface coated with nitrocellulose. In this embodiment, the "wall" of the well has vertical openings extending from the planar plate to the bottom of the well. As shown in FIG. 1A, the openings in the "wall" would allow liquid to flow in and out of the well with less impedance, while the sections between the openings connect the membrane with the planar surface. Indeed, a QDB plate can be a structure that supports the membrane and connects the supported membrane to a planar surface. For example, the membrane can be supported on a support structure (e.g., a ring, a plate) while one or more posts may link the supported membrane and the planar surface.

After the sample is loaded on the membrane, the QDB plate is dried at room temperature for 1 hour or 37° C. for 15 mins. The QDB plate is then inserted into a multi-well plate (96-wells in this embodiment) to form a plate assembly (FIG. 1F).

FIG. 1G illustrates steps of blocking and labeling, as exemplified in the following. The multi-well plate is loaded with a blocking buffer (5% nonfat milk in TBST buffer). The membranes in the QDB plate were inserted into the regular well plate to be immersed in the blocking buffer for 1 hour and then washed. The QDB plate is then incubated with primary antibody (1° antibody) either overnight at 4° C. or for 2 hours at room temperature before the QDB plate is washed three times in TBST for 5 mins each. After washing, the QDB plate is incubated with a secondary antibody (2° antibody) pre-labeled with HRP for 1 hour at 1:1000.

In the quantification step, the QDB plate is washed again with TBST buffer for three times for 5 mins each, and inserted into a 96-well plate loaded with ECL substrate for 1 min (FIG. 1H). The QDB plate is then transferred into a white 96-well plate and quantified directly using a microplate reader with the "plate with cover" option chosen (FIG. 1I). Signals obtained by the reader are compiled and analyzed (FIG. 1J).

There are multiple alternative processes for the steps of blocking, antibody incubation and washing, i.e., FIG. 1G. For example, if only one primary antibody is used, the steps described in FIG. 1G can be carried out in one container.

In some embodiments, the blocking buffer may be 5% non-fat milk, or 3% BSA in either PBS or TBS buffer supplemented with 0.1% Tween 20. The membrane may be dried in the air at room temperature, or in a ventilated heated place to facilitate the process.

Labeling and detection of the signals may include enzymatic coupling of the antibody or a molecule, radiolabeling with antibody, or labeling the antibody or a molecule with fluorescent dye, and the readout can be detected either through visual inspection in a color reaction, or through X-ray film when antibody is labeled with radioactive materials or with a reporter enzyme.

In this embodiment of the QDB process, since the membrane in each individual subunit in the QDB plate may be separated from each other, the QDB plate may accommodate different samples at the same time. Furthermore, such individual samples, after being labeled, may be quantified individually, independent from other samples.

In a further embodiment, the antibody is first labeled with horseradish peroxidase, which converts ECL substrate into chemiluminescent signals. The signal intensity is manifested using a chemiluminescence sensitive film or a scanner, and quantified indirectly through densitometric analysis. The QDB analysis reads the signal from each sample directly using a microplate reader. The signals intensity may be digitized directly without first registering the signals as images using a film or a scanner.

In contrast, in both Dot blot and Western blot analyses, the signal detection is based on images acquired using a film or a scanner. It is difficult to accurately report the linear range of the analysis after the image conversion process. In the QBD analysis, a dose curve can be established first, which enables an operator to load the amount of samples within the linear range of the dose curve.

Still, in blot and Western blot analysis, the amount of sample used for analysis is largely based on the experience of the researcher. In most cases, at least 20 μg to 100 μg per sample is required. In comparison, in the QDB process, due to increased sensitivity, less than 10 μg per sample, for example 0.1 μg to 3 μg per sample, is sufficient to yield accurate results.

Comparing with ELISA, which typically has a protein binding capacity of less than 1 μg/cm$^2$, the QDB process employs membranes, which have a much better binding capacity, e.g., about 100 to 200 μg/cm$^2$. Furthermore, one distinguishing feature of the QDB plate is that its individual subunit allows the buffer fluid to easily flow in and out of the subunit so that the membrane in the sub-unit is more thoroughly washed than in the closed wells in ELISA. This allows effective washing of the membrane, reducing the background noises in the detection step.

As used therein, "membrane" is to be taken into its broadest context. A membrane can be any material with comparable binding capacity with PVDF or nitrocellulose membrane and sufficient surface porosity to allow access by detection antibodies and a suitable surface affinity to bind antigen. The membrane may be coated or supported on a planar or a curvilinear surface of a substrate so that one side of it is in contact with the substrate. The membrane may be supported on a hollow support so that both sides of the membrane is exposed and accessible. All these materials may be used in suitable shapes, such as films, sheets, or plates; or, they maybe coated onto or bonded or laminated to appropriate insert carriers, such as paper, glass, plastic materials or fabrics. For example, a membrane can be, but not limited to, nitrocellulose membrane or PVDF membrane.

There is no physical limitation of the shape and structure of the membrane, as long as it provides binding surface for antigen. The membrane within each membrane unit can be continuous or discontinuous. It can be in one piece, or it can be in more than one piece, as long as it binds the same sample within individual membrane unit.

As used herein "reporter enzyme" is to be taken in its broadest context. A reporter enzyme can be any modification of the antibody in immunodetection assay with the purpose to aid the detection of the antibody. For example, a report enzyme can be, but not limited to, antibody directly labeled with radioactive isotope like Iodide 125, or reporter enzymes like alkaline phosphatase or horseradish peroxidase. The detection of the amount of reporter enzymes associated with antibody is through the formation of a detectable product as the readout of the amount of reporter enzymes in the detection reaction. The product can be radioactive, luminescent, fluorescent, or a product with characteristic absorbance or reflection spectrum in the visible or outside the visible range. When a complement is used to detect the bound antigen-antibody complex, it may either be labeled in any one of the above ways, or be detected in turn by a specific anti-complement antibody.

A report enzyme can be, but not limited to, antibody indirectly labeled with radioactive isotope like Iodide 125, or reporter enzymes like alkaline phosphatase or horseradish peroxide. Antibody can be, but not limited to, indirectly labeled through a secondary antibody, and the secondary antibody is directly or indirectly labeled with radioactive isotope like Iodide 125, or reporter enzymes like alkaline phosphatase or horseradish peroxide. In one embodiment, the secondary antibody is labeled with biotin, and indirectly further labeled with a horseradish peroxide through a streptavidin molecule.

As used herein "antigen" and an "antibody" are to be taken in their broadest context. An "antigen" can be a molecule, a cell, a virus, or a particle. The term "antigen" may be used to refer to a chemical compound, a peptide, a protein, an RNA, a DNA, a cell (proteins released in situ), or a virus particle (proteins released in situ) or any molecules that may evoke the production of one or more antibodies by a host animal, including human. An antigen may also be a product comprising any two or more of the molecules or moieties crosslinked together. An antigen can exists either in a pure form, or it can exist in a mixture. An antigen can be in a modified form (e.g., modified by a chemicals) or be in an unmodified form.

Reference herein to an "antibody" is to be taken in its broadest context. An "antibody" is a polypeptide that binds to "an antigen". An antibody includes, but is not limited to, a traditional antibody, a fragment of a traditional antibody containing an antigen binding site, a recombinant antibody containing an antigen binding site, a protein which binds to an antigen, and a product that comprises of crosslinking any two or more of the above. An antibody can exist either in a pure form, or in a mixture. An antibody can be in a modified form (e.g., modified by a chemical) or be an unmodified form.

Experimental Methods

The disclosures are illustrated in the following non-limiting examples. Modifications of the examples may be made without departing from the spirit and scope of the disclosures.

General reagents for tissue culture related work were purchased from Thermo Fisher Scientifics (Waltham, Mass., USA), including cell culture medium and culture dishes. HEK293 cells were purchased from the Cell Bank of Chinese Academy of Sciences, Shanghai, China. QDB plates were obtained from QDB Biotechnique Co. Ltd, Yantai, China. The protease inhibitors were purchased from Sigma Aldrich (St. Louis, Mo., USA). All other chemicals were purchased from Sinopharm Chemicals (Beijing, P. R. China). Mouse Strains: TRAMP mice and their wild type littermates were purchased from Jackson Laboratory (www-.jax.org). These mice were from a C57BL/6 origin and obtained from C57-x C57-matings. Animals were supported under a 12/12 hours light-dark cycle with natural drink and food. All animal procedures were approved by the ethical review board of Binzhou Medical University (ER #2016-19). The genotype of animals and confirmation of tumorigenesis were described elsewhere.

Antibodies: Rabbit anti-tubulin (YT-0183), rabbit anti-ApoE (YT-0273) antibodies were purchased from Immunoway, Suzhou, P. R. China, Rabbit anti-p65 (SC-372, C20, F0414), Rabbit anti-CDK4 (sc-260, c22, A0314) were purchased from Santa Cruz Biotechnology, Inc. (Santa Cruz, Calif., USA). Rabbit anti-CAPG (14213-T52) antibody was purchased from Sino Biologic Inc. Beijing, P. R. China.

Screening of stable clones: For construction of constitutive expressed RNA interference (RNAi) constructs, pGreenpuro plasmid from System Biosciences Inc. (Palo Alto, Calif., USA) was used by following the manufacturer's instructions using a targeting sequence 5' GGACATAT-GAGACCTTCAAGA 3' against p65 to create ShRNA-p65 plasmid or target sequence 5' GTGCGTTGTTAG-TACTAATCCTATTT3' against luciferase to create ShRNA-Luciferase plasmid. ShRNA-p65 and ShRNA-Luciferase plasmids were used to transfect HEK293 cells at $5 \times 10^5$/dish in two 60 mm dishes respectively using Fugene 6 transfection reagent by following manufacturer' instructions. Cells were allowed to grow for two days in growth medium (DMEM medium supplemented with 10% fetal bovine serum) before they were changed into fresh selection medium (growth medium supplemented with 5 µg/mL puromycin).

The selection process continued by exchanging the selection medium every 3 to 4 days until visible clones could be seen with naked eyes. Individual clones were picked up by trypsin digestion using Cloning cylinder from Sigma, and transferred to two parallel 24 well plates at 1:9 ratio, and labeled by the same clone number with plate A for 24 well plates with more cells, while B for those with less cells. The cells were allowed to growth continuously in selection medium until the plate A reached confluence.

Total cell lysates were prepared in plate A by adding lysis buffer (50 mM Hepes, pH 7.4, 137 mM NaCl, 5 mM EDTA, 5 mM EGTA, 1 mM $MgCl_2$, 10 mM $Na_2P_2O_7$, 1% Triton X-100, 10% glycerol, supplemented with protease and phosphatase inhibitors (100 mM NaF, 0.1 mM phenylmethylsulfonyl fluoride, 5 µg/mL pepstatin, 10 µg/mL leupeptin, 5 µg/mL aprotinin) to the plate directly. Total cell lysates were prepared by collecting supernatant after 5 min of centrifugation, and sample buffers were added directly to the supernatant for the QDB analysis.

For plate B, representative clones based on the result from QDB analysis of plate A were transferred to two 60 mm dishes at $2 \times 10^5$/dish, and cells were allowed to grow for two days in the selection medium before they were either harvested for preparation of total cell lysate and measurement of protein concentration (see next section), or for storage in liquid nitrogen.

Cell and tissue extractions: For HEK293 cells, cells were harvested and lysed in lysis buffer by pipetting up and down 50 times. Supernatants were collected after 5 min of centrifugation at 8000× g, and protein concentration was determined by using Pierce BCA protein assay kit from Thermo Fisher before they were re-suspended in sample buffer for Western blot analysis. For preparing tissue lysates from mouse livers and prostates, tissues were sliced into microcentrifuge tubes pre-aliquoted with 300 mL lysis buffer with protease inhibitors. Tissues were minced with a handhold tissue homogenizer for 1 minute before the microcentrifuge tubes were subjected to centrifugation at 8000× g for 5 min. The upper supernatant from each tube was collected for measurement of protein content and for Western blot analysis using Pierce BCA protein assay kit from Thermo Fisher.

QDB process: Prepared total lysate from 0.1 µg to 4 µg/unit, based on dose curve of the antibody used in the analysis, was applied directly on individual membrane of the QDB plate. The QDB plate was left either at 37° C. for 15 mins or at room temperature for 45 mins to allow membrane to dry completely before it was dipped into the transfer buffer briefly. The QDB plate was rinsed with TBST (137 mM NaCl, 2.7 mM KCl, 20 mM Tris, pH 7.4, plus 0.1% Tween-20) for 3 times, and blotted with blocking buffer (5% non-fat milk in TBST) in one container. The QDB plate was incubated with primary antibody either overnight at 4° C. or for 2 hour at room temperature in either one big container if the whole plate was blotted with same antibody, or into a 96-well plate with different antibodies within different wells. The QDB plate was washed three times with TBST, and incubated again with the secondary antibody for 2 hour before the plate was washed again for three times with TBST. The QDB plate was inserted into a 96-well plate loaded with 100 µL/well ECL substrate solution for 1 minute before it was inserted into a white 96-well plate for chemiluminescence signal quantification using a Tecan Infiniti 200 pro microplate reader. The "plate with cover" option on the control panel was checked to avoid incompatibility due to raised combined plates during the measuring process.

Statistical analysis: Data were presented as mean±SEM, and analyzed with the two-tailed Student's t-test between two groups. The q-q plot was performed with SPSS v22.0 (IBM, Chicago, Ill.).

EMBODIMENTS

Example 1

Figure 2:
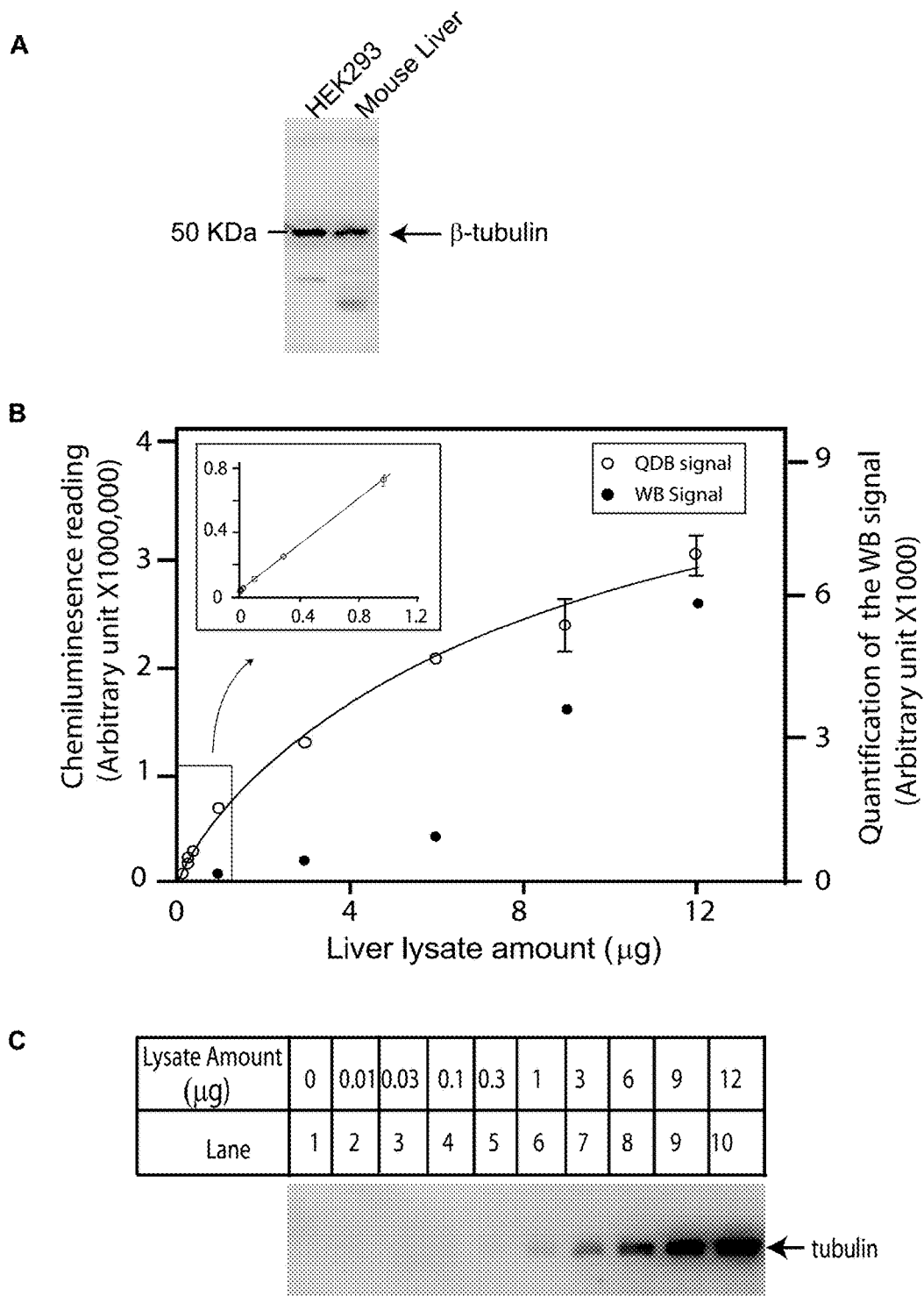
FIG. 2 shows an example of examining the specificity of the antibody and establishing the dose curve of the same antibody in QDB analysis using a rabbit anti-tubulin antibody.

Mouse liver lysates were prepared as described in the experimental methods, and total cell lysates were resuspended in 4×SDS sample buffer (Laemmli buffer) and heated for 5 minutes at 75° C. A Western blot analysis was performed using the rabbit anti-tubulin antibody with HEK293 cells and mouse liver lysate at 40 µg/lane. FIG. 2A shows that there was only one band of expected size on the membrane, corresponding to β-tubulin.

mouse liver lysate was diluted to obtain samples from 0.1 mg/unit to 12 mg/unit. Samples of 3 µl per unit were applied to the nitrocellulose membrane bottom in the individual unit of QDB plate—the same type as shown in FIG. 1A. The samples were allowed to dry at room temperature for 45 min.

The QDB plate loaded with samples was blocked with a blocking buffer (5% no-fat milk in Tris buffered saline supplemented with 0.1% of Tween 20 (commonly known as "TBST") for 1 hour before the samples were exposed to a rabbit anti-tubulin antibody in blocking buffer at 1:2000 dilution overnight.

After 3×5 minutes wash with the TBST buffer, the QDB plate was incubated with a Donkey anti-Rabbit secondary antibody pre-labeled with horseradish peroxide for 1 hour. After another 3×5 minutes wash with the TBST buffer, the QDB plate was inserted into a 96-well plate, and 100 µl of a chemiluminescence substrate mix was added according to manufacturer' instructions. The QDB plate was left in the 96-well plate for one minute before it was transferred to a white 96-well plate for quantification using a Tecan microplate reader.

FIG. 2B shows two dose curves of the liver lysate sample with anti-tubulin antibody. Each data points is the average of triplicate with SEM. The circles represent signals obtained in the QDB process ("the QDB signal") while the solid dots represent signals obtained using Western blotting ("the WB signal"). The insert in FIG. 2B shows the QDB dose curve in the range from 0 to 1 µg, which exhibit a linear relation between the chemiluminesence signals and the amount of lysate with the coefficient of variance ($R^2$) at 0.999. From 1 µg to 12 µg, the QDB signals gradually approach saturation, and the QDB dose curve is no longer linear.

The same amount of lysate were used in the Western blotting. The WB signals are shown in FIG. 2C, which were converted digitally using Image Studio Digits from Li-Cor (Lincoln, Nebr., USA) and plotted in FIG. 2B as the solid dots. However, the WB dose curve appears irregular with $R^2=0.907$. It is difficult to determine the linear range in the WB dose curve with much confidence. In comparison, the QDB analysis determined the linear application range of the assay with a much higher accuracy ($R^2=0.999$).

This example demonstrates how to establish the specificity of the detection antibody, and how to establish the linear range of the QDB assay based on the samples to be analyzed using a specific antibody. By comparing the QDB analysis and the Western blot analysis using same samples under same experimental conditions, the experiments demonstrated the quantitative nature of QDB analysis in contrast to the semi-quantitative nature of Western blot analysis.

Example 2

Figure 3:
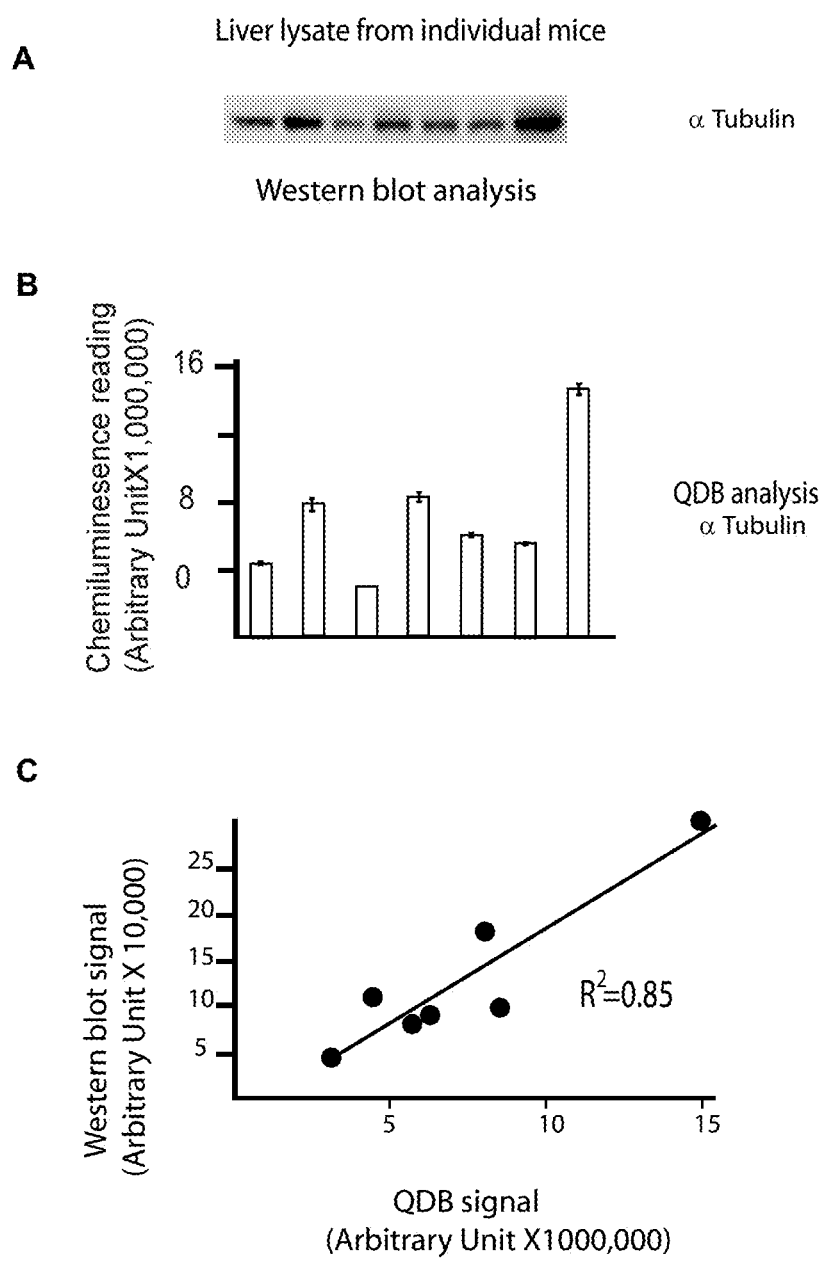
FIG. 3 shows QDB analysis results using a rabbit anti-tubulin antibody to measure tubulin content in mouse livers of 7 mice.

In this experiment, roughly similar size liver slices from 7 mice were prepared and homogenized as described in the Materials and Methods section. Equal amount of liver lysate (20 µL, representing 40 µg total protein/lane) from each mouse was used for the Western blot analysis. FIG. 3A shows the results from Western blot analysis of α-tubulin contents in these seven liver lysates. The same mouse liver lysates used for FIG. 3A were loaded to the individual membrane units of the QDB plate at 0.5 µL/unit or 1 µg total protein/unit in triplicate. The result is the average of the triplicate from each mouse±SEM. FIG. 3B shows the QDB signals for α-tubulin contents. The results of Western blot analysis and QDB analysis using the lysate from the same mouse were aligned to each other for comparison purpose. FIG. 3C plots the WB signals (digitized using Image Studio Digits) against the QDB analysis. The simple linear regression analysis was performed, which found a coefficient of variations ($R^2$) of 0.85. Mouse number refers to the assigned number of individual mice for recordkeeping.

Together with Example 1, Example 2 demonstrated a complete process of QDB analysis, benchmarked with Western blot analysis.

Example 3

Figure 4:
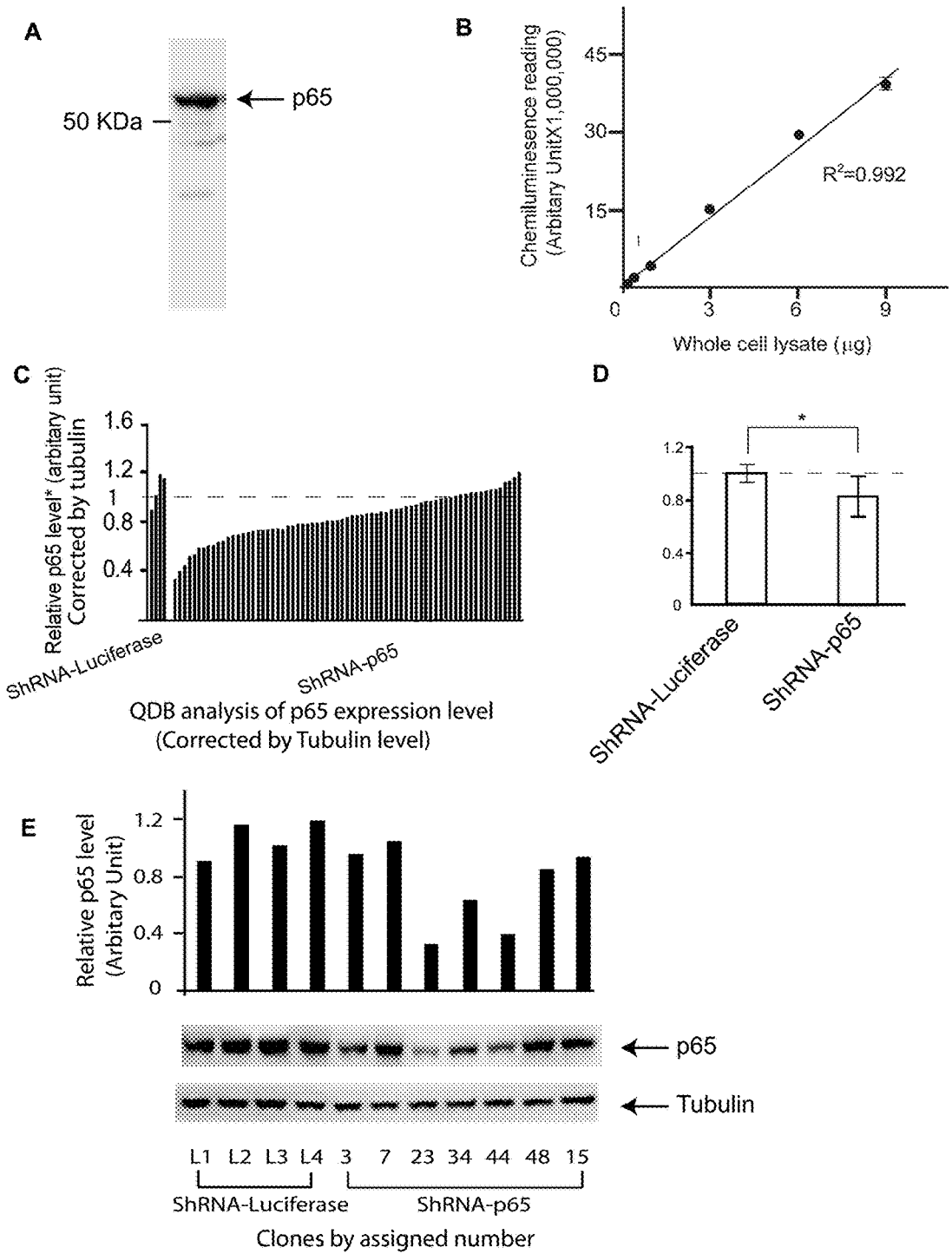
FIG. 4 showed an example of large scale analysis of the content of a specific protein molecule at cellular level using QDB analysis.

FIG. 4A shows the WB signal using rabbit anti-p65 antibody in the HEK-293 whole cell lysate. An HEK293 whole cell lysate was prepared as described in the Experimental Methods section. The whole cell lysate of 50 µg/lane was used for Western blot analysis using a rabbit anti-p65 antibody from Santa Cruz Biotechnology Inc. The whole membrane was scanned using a blot scanner from Li-Cor.

To construct the dose curve, the HEK293 whole cell lysate was serially diluted and applied to a plurality of membrane units in the QDB plate in triplicate. The loaded QDB plate was processed as described in the Experimental Methods section and quantified through ECl reaction using a Tecan microplate reader. FIG. 4B shows the QDB dose curve. A simple linear regression analysis found the coefficient of variations to be 0.992 in the range from 0 to 9 μg.

HEK293 cells were transfected with ShRNA-p65 or ShRNA-Luciferase using Fugene 6 transfection reagent. Stable clones were selected using puromycin at 5 μg/mL from cells transfected with ShRNA-p65 (p65 clones) or ShRNA-Luciferase (Luciferase clones) until they were visible with naked eyes. Clones were selected and transferred to two 24-well plates (Plate A and Plate B) at 1:9 ratio. Luciferase clones were labeled as L1 to L5, while p65 clones were labeled sequentially.

The 24-well plates with a larger portion of cells (Plate A) were monitored daily until the cells reached confluence in individual well. These cells were collected to prepare cell lysates as described in the Experimental Methods section. The whole cell lysate from individual clone was used for QDB analyses of tubulin and p65 levels. The relative level of p65 (i.e., the ratio of p65 level over tubulin level) was used to compare endogenous p65 expression levels in each clone, using the average of the p65 expression levels in luciferase clones as 1. The results are presented in FIG. 4C, in which each data point is an average of three independent experiments in triplicates.

FIG. 4D compares the relative p65 levels between Luciferase and p65 clones. p65 clones and luciferase clones were first isolated as described in the Experimental Method section. The relative level of p65 was calculated from individual clones and averaged to compare endogenous levels of p65 between luciferase and p65 clones at the population level. For comparison purposes, the average of 5 luciferase clones was arbitrarily set as 1. *, $p<0.05$ using student T-test. The relative level of p65 is about 0.8.

Meanwhile, representative clones were picked up from the 24-well plate with less cells (Plate B) based on the results shown in FIG. 4C and transferred to 60 mm dishes. Once the cells reach a sufficient number, they were used for Western blot analysis using anti-p65 and anti-tubulin antibodies. The lower panels in FIG. 4E shows the WB signals for p65 and tubulin, respectively. Results from QDB analyses of same cells in FIG. 4D are re-plotted in the top panel in FIG. 4E. Screening stable clones at cellular levels is a common practice in biological research.

In this example, we performed a process of screening stable clones from HEK293 cells transfected with RNAi plasmids to demonstrate that it is feasible to conduct the QDB analysis at the cellular level.

Example 4

This group of experiments evaluated the relative amount of CAPG protein in mouse prostate tissues. Lysates prepared either from HEK293 cells or mouse prostate tissue at 50 μg/lane were used for Western blot using a rabbit anti-CAPG antibody. The whole membrane was scanned using a blot scanner from Li-Cor. The insert in FIG. 5A shows the WB signal from the antibody validation.

Figure 5:
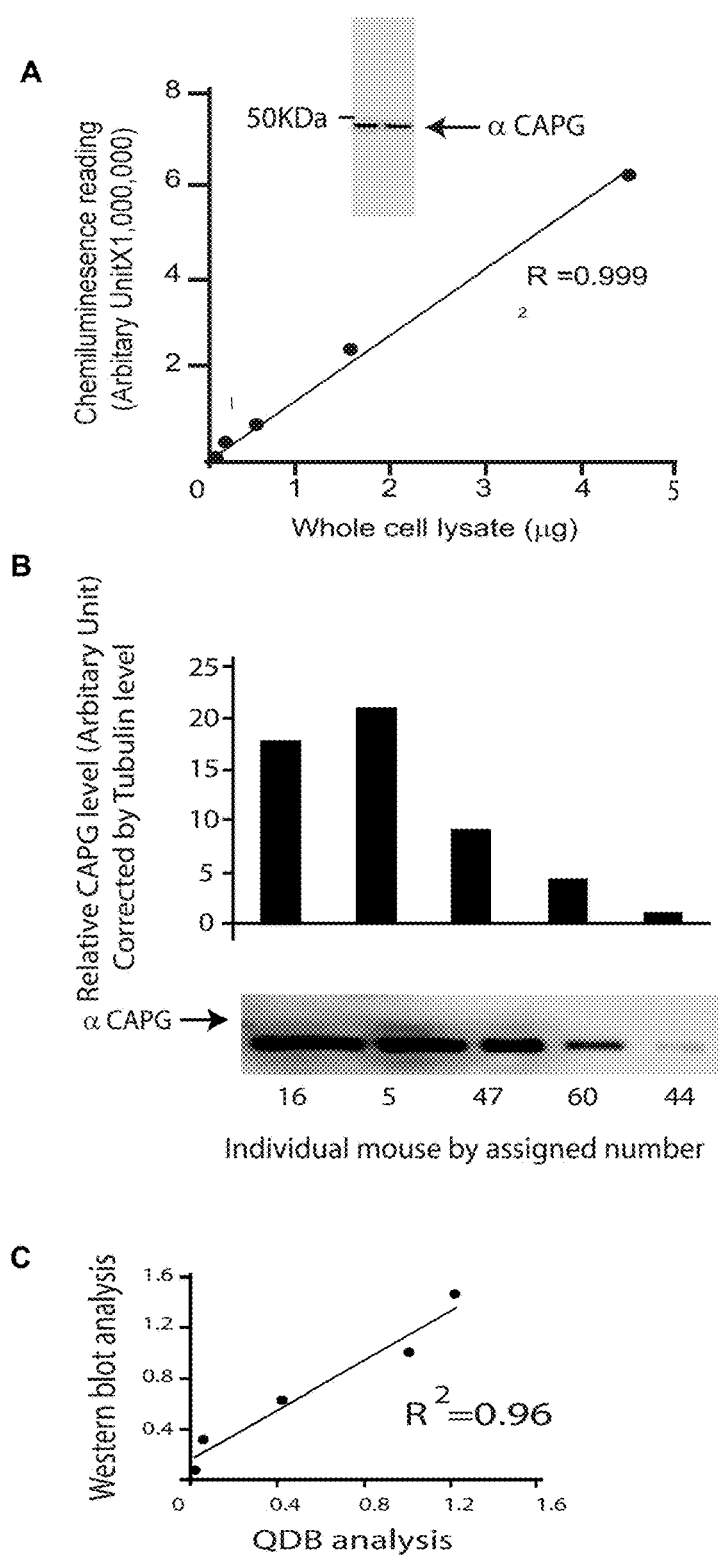
FIG. 5 shows an example of a QDB analysis of the content of a specific protein molecule in animal tissues, benchmarked with Western blot analysis.

FIG. 5A is a dose curve based on the QDB signals. Pooled lysate prepared from mouse prostate tissues was serially diluted from 0.1 μg to 4.8 μg, which were used for QDB analysis using the rabbit anti-CAPG antibody.

Benchmarking the QDB analyses of relative CAPG levels with Western blot analysis. Prostate tissues were collected from individual mice, as indicated by the assigned number. For the QDB analysis, prostate tissue lysates of 2 μL (around 1 μg total protein lysate per sample) in triplicate were used for the measurement of both tubulin and CAPG levels in individual mouse, as well as the relative CAPG level of individual mice. The relative CAPG level is expressed as the ratio of CAPG level over tubulin level, shown in the top panel in FIG. 5B. Meanwhile, the amount of lysate of each sample used for Western blot analysis was adjusted based on the result of QDB analysis of tubulin levels of these samples to allow equal loading. Subsequently, CAPG levels in these samples were examined using Western blot analysis. For lysate prepared from mouse #44, about 30 μg total tissue lysates were used. The WB signals were shown in the bottom panel in FIG. 5B. The WB signals were digitized using Image Studio Digits from Li-Cor. FIG. 5C shows the good correlation between WB signals and QDB signals, having a coefficient of variations ($R^2$) of 0.96.

This example demonstrated the reliability of the QDB method in evaluating CAPG contents in different mouse prostate tissues, benchmarked with Western blot analysis.

Example 5

This group of experiments compared relative CAPG levels in prostate tissues of the wild type (WT) and Transgenic Adenocarcinoma of the Mouse Prostate (TRAMP) mice. Prostate tissues were collected from WT and TRAMP mice. Whole tissue lysates were prepared and used for QDB analyses of CAPG and tubulin levels. The relative CAPG level, expressed as the ratio of CAPG level over tubulin level, was calculated and averaged by the genotype. The results were the average of three independent experiments, with each sample in triplicate in each experiment (p=0.6723 based on student T-test). The relative CAPG levels for the WT mice and the TRAMP mice are 8.243±0.372 au and 11.835±0.238 au, respectively (au, arbitrary unit), as shown in FIG. 6A.

Figure 6:
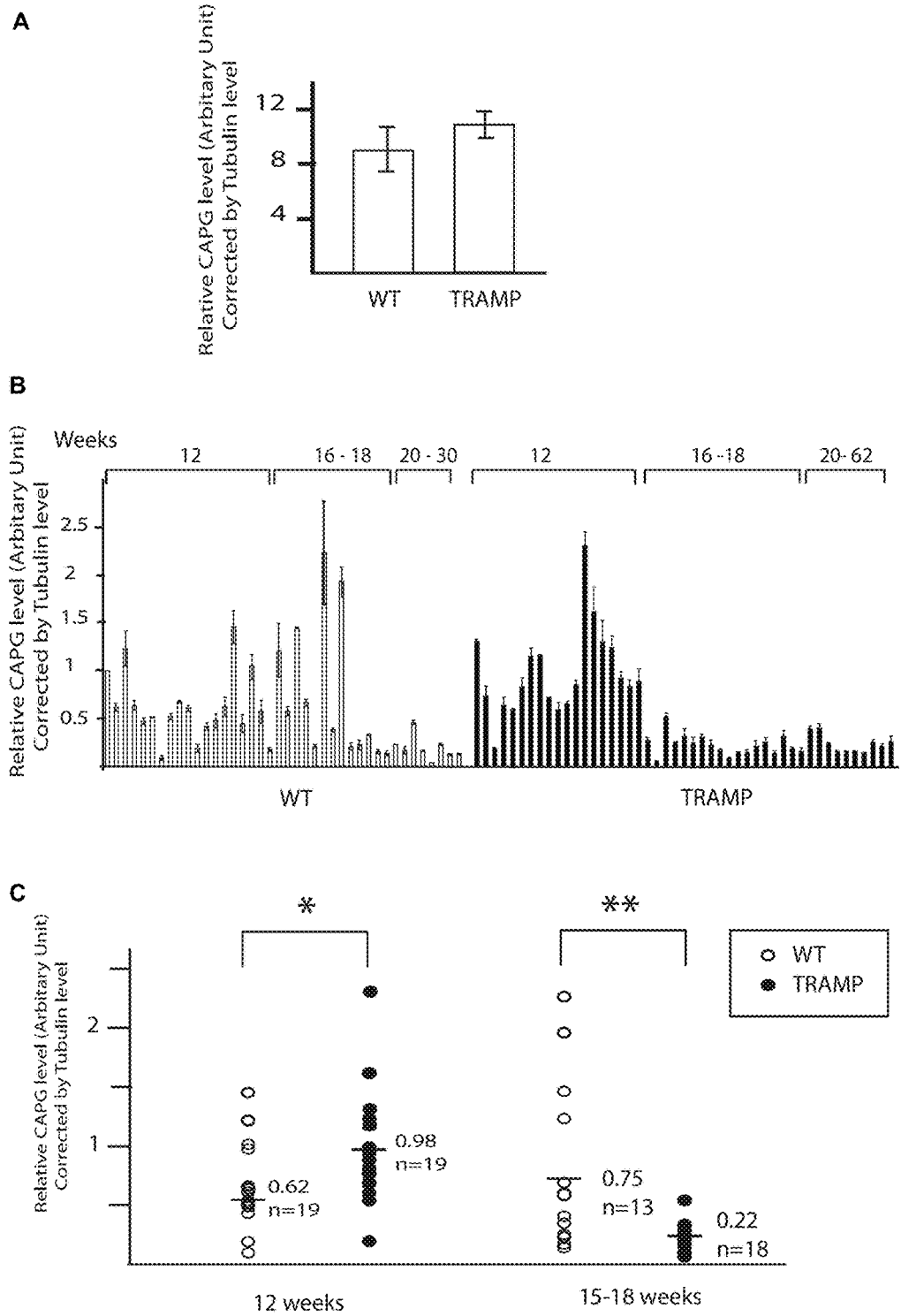
FIG. 6 shows an example of a large scale analysis of the content of a specific protein molecule in animal tissues using QDB analysis, and how their results could be analyzed from different angles.

The same QDB results were re-plotted against their ages and phenotypes, as shown in FIG. 6B.

Stratified analysis of relative CAPG levels by age in the WT and TRAMP mice is presented in FIG. 6C. The two groups of data on the left side are averages of 19 mice of WT and 19 TRAMP mice among 12 weeks old mice, while the two groups on the right are averages of 18 WT mice and 13 TRAMP mice among mice of 15-18 weeks old. *, $p<0.05$, ** $p<0.01$ based on student t-test.

The results indicates that the average CAPG levels at 12 weeks: WT, 0.643±0.082, TRAMP, 0.963±0.107; and 15-18 weeks, WT, 0.685±0.133, and TRAMP, 0.250±0.025.

This is an example of a large scale QDB analysis of a specific protein molecule in animal tissues. FIGS. 6B and 6C further demonstrated that how the data presented in FIG. 6A can be analyzed and presented in different ways.

Example 6

Two types of QDB plates (Type A and Type B) were used in this study. Type A plate is shown in FIG. 1A, which provides two notches in the vertical ring surrounding the membrane. Type B plate has the same structure as Type A except that there is no opening in the vertical rings surrounding the membrane. As such, Type A plate allows the fluid to flow in and out through the notches in the vertical rings with ease, facilitating the washing of the membrane.

Type B plate, on the other hand, would have a thin layer of the fluid accumulating inside the vertical ring, impeding solution exchanges between the membrane surface and the washing fluid.

An anti-ikB antibody was used in studying the dose response. Each of the Type A plate and the Type B plate has 48 membrane units so that both were fit into a 96-well plate. Mouse liver lysates were prepared from frozen tissues using a handheld homogenizer in lysis buffers containing protease inhibitors as described in Zhang, J. 2007. The protein concentration was measured using the BCA method. Total cell lysates were resuspended in 4×SDS sample buffer (Laemmli buffer) and heated for 5 minutes at 75° C. Mouse liver lysate was serially diluted, and applied to individual membrane unit of both Type A and Type B plates. The samples were allowed to dry at room temperature for 45 min. Both plates were blocked with a blocking buffer (5% no-fat milk in Tris buffered saline supplemented with 0.1% of Tween 20 (commonly known as "TBST") for 1 hour before the samples were exposed to a rabbit anti-tubulin antibody in blocking buffer at 1:2000 dilution overnight. Followed by 3×5 minutes wash with the TBST buffer, the QDB plate was incubated with a Donkey anti-Rabbit secondary antibody pre-labeled with horseradish peroxide.

After another 3×5 minutes of wash with the TBST buffer, both Type A and Type B were inserted into a 96-well plate. 100 μL chemiluminescence substrate mix was added according to manufacturer' instructions. The plates were left in the 96 well plate for one minute before they were transferred to a white 96 well plate. The combined plates are placed in a Tecan microplate reader for quantification by selecting the option "plate with cover" on the operational menu of the microplate reader.

Figure 7:
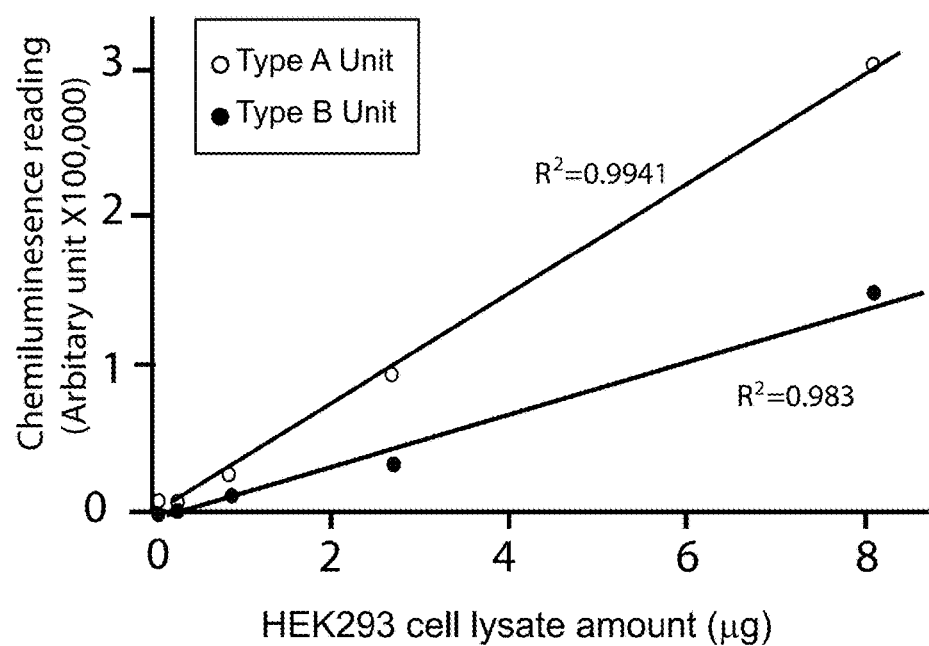
FIG. 7 shows effect of different configurations of the QDB plate on the result of QDB analysis.

The dose curves are presented in FIG. 7. The dose curve using Type A plate shows more than twice the signal intensity as compared with the dose curve using Type B plate. Type A plate also produced signals with a better linearity ($R^2=0.9941$ for Type A vs. $R^2=0.983$ for Type B). This effect may be attributable to the fact that Type A plate allows more effective washing, which better cleans the membrane and reduces the noise level.

This group of experiments demonstrates that thorough washing improves the data quality.

Example 7

Figure 8:
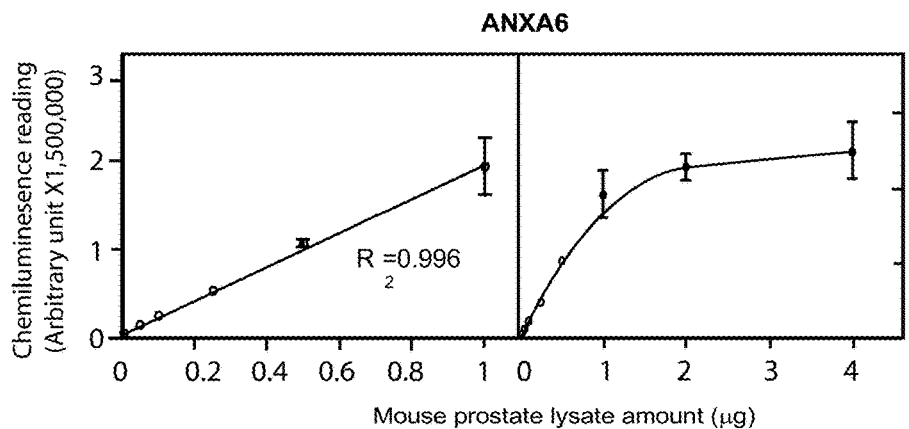
FIG. 8 shows dose curves of several detection antibodies to illustrate that QDB analysis is highly antibody dependent.
Figure 8:
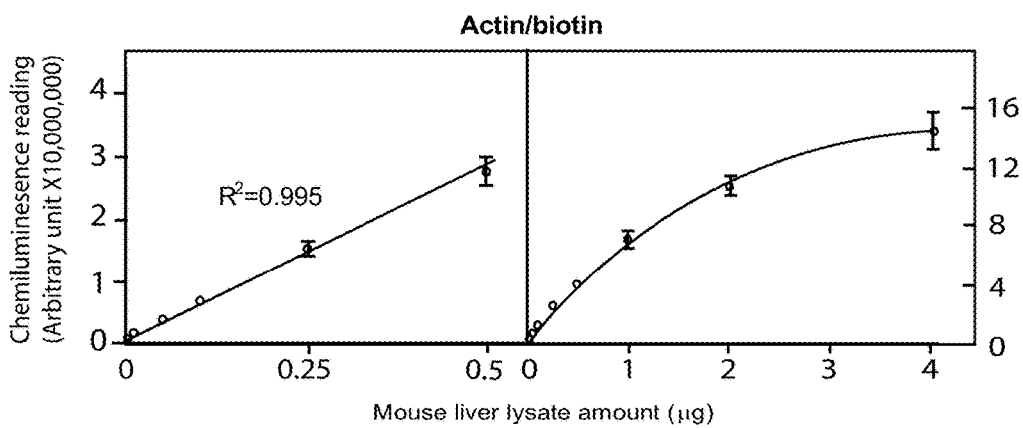
Figure 8:
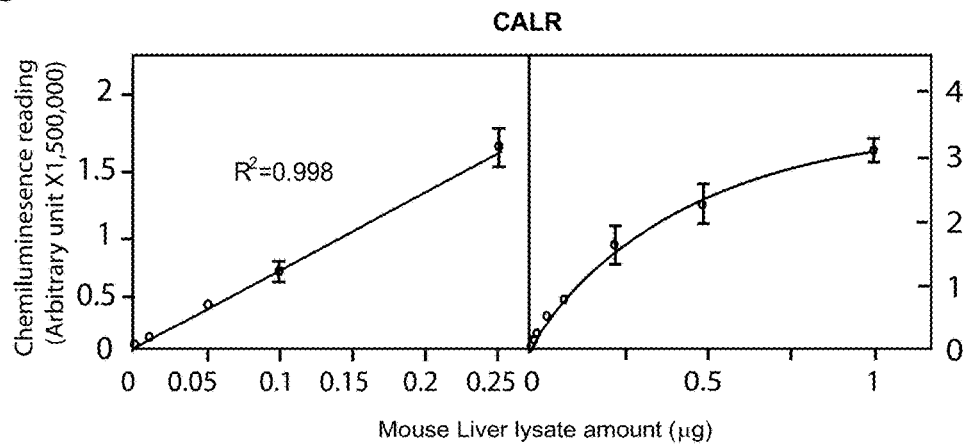

This group of experiments investigates linear ranges of different antibodies in QDB analysis. FIG. 8A shows side-by-side the overall QDB dose curve (0 μg to 4 μg) and the linear range therein (0 μg to 1 μg) for a mouse prostate lysate using anti-ANXA6 antibody. The dose curve in this linear range has a coefficient of variations $R^2=0.996$. Likewise, FIG. 8B shows the overall QDB dose curve and its linear range of a mouse liver lysate using anti-actin antibody. The signal was enhanced by coupling with a biotin-streptavidin system. In this case, the linear range is 0 μg to 0.5 μg with $R^2=0.996$, allowing smaller sample sizes in the QDB analysis.

FIG. 8C shows the overall QDB dose curve (0 μg to 1 μg) and its linear range (0 μg to 0.25 μg) of a mouse liver lysate using anti-CALR antibody. The linear range has a coefficient of variations $R^2=0.998$.

Our results shows that the dose curves of detection antibody is different from each other. The evaluation of the detection antibody and the establishment of the dose curve of the detection antibody is necessary prior to the large scale QDB analysis.

Variations of the embodiments are possible. For example, the current QDB method can be used to perform enzyme-linked immunosorbent assay (ELISA). In such a process, an equal amount of antibody A is first applied to the bottom of the individual membrane units of QDB plate to bind to the membrane. The QDB plate is then blocked with a blocking buffer. After the blocking step, one or more samples of interest are applied to the individual membrane unit of the QDB plate. After washing, an equal amount of antibody B labeled directly or indirectly labeled directly or indirectly with a reporter enzyme is applied to the individual membrane unit of the QDB plate. The plate is washed again. The immunocomplexes formed in each membrane unit of the QDB plate are measured directly or indirectly with a detection reagents.

In addition to enzyme labels such as HRP, AP or glucose oxidase, embodiments in this disclosure may employ any available immunoassay labels, including: radioactive isotopes, DNA reporters (e.g., in real-time immnoquantitative PCR), fluorogentic reporter (e.g., phycoereythrin), electrchemiluminescent tags, etc.

Embodiments in this disclosure may employ any commercially available microplate readers. The microplate readers may use different detection techniques for signal detections, e.g., absorbance, fluorescence, chemiluminescence, time-resolved fluorescence, fluorescence polarization, etc.

It is to be understood that the exemplary embodiments described herein are that for presently preferred embodiments and thus should be considered in a descriptive sense only and not for purposes of limitation. Descriptions of features or aspects within each embodiment should typically be considered as available for other similar features or aspects in other embodiments.

LIST OF REFERENCES

The following references, patents and publication of patent applications are either cited in this disclosure or are of relevance to the present disclosure. All documents listed below, along with other papers, patents and publication of patent applications cited throughout this disclosures, are hereby incorporated by reference as if the full contents are reproduced herein.
1. Burnette, W. N. "Western Blotting": Electrophoretic transfer of proteins from Sodium Dodecyl sulfate-Polyacrylamide gels to unmodified nitrocellulose and radiographic detection with antibody and radioiodinated protein A. Analytical Biochemistry (1981) V. 112, pp. 195-203.
2. Hawkes, R Niday, E., Gordon, J. A Dot-immunobinding assay for monoclonal and other antibodies. Analytical Biochemistry (1982) V. 119, pp. 142-147.
3. Engvall, E., Perlmann, P. Enzyme-linked immunosorbent assay (ELISA) Quantitative assay of immunoglobulin G. Immunochemistry (1971) V. 8, pp. 871-874.
4. Engvall, E., Jonsson, K., Perlmann, P. Enzyme-linked immunosorbent assay II. Quantitative assay of protein antigen, immunoglobulin G, by means of enzyme-labeled antigen and antibody-coated tubes. Biochemica et biophysica acta (1971) V. 251, pp. 427-434
5. Engvall, E., Perlmann, P. Enzyme-linked immunosorbent assay, ELISA III. Quantitation of specific antibodies by enzyme-labeled anti-immunoglobulin in antigen-coated tubes. The journal of Immunology (1972) V. 109, pp. 129-135.

6. Yalow, R. S., Berson, S. A. Immunoassay of endogenous plasma insulin in man. Journal of Clinical Investigation (1960) V. 39, pp. 1157-1175.
7. Zhang, J. The direct involvement of SirT1 in insulin-induced insulin receptor substrate-2 tyrosine phosphorylation Journal of Biological Chemistry (2007). V. 282, pp. 34356-34364.
8. Paweletz, C. P., Charboneau, L., Bichsel, V. E., Simone, N. L., Chen, T., Gillespie, J. W., Emmert-Buck, M. R., Roth, M. J., Petricoin III, E. F., Liotta, L. A. Reverse phase protein microarrays which capture disease progression show activation of pro-survival pathways at the cancer invasion front. Oncogene (2001). V. 20, 1981-1989.

I claim:

1. A method for detecting an antigen, comprising:
   binding the antigen to a plurality of membrane units, wherein:
      each of the plurality of membrane units is individually compartmentalized to ensure signal emitted therefrom to be individually acquired, and
      each membrane unit is affixed to one of a plurality of corresponding supports,
      wherein said each corresponding support can hold said membrane unit;
   selecting a primary antibody that interacts with the antigen;
   binding the primary antibody to the antigen to form immunocomplexes so that each of the plurality of membrane units have immunocomplexes attached thereto;
   causing the immunocomplexes to emit signals; and
   detecting, from each of the plurality of membrane units, the signal emitted by the immunocomplexes attached thereto.

2. The method of claim 1, wherein the immunocomplexes are labelled with a labelling substance selected from a group consisting of reporter enzymes, radioactive isotopes, DNA reporters fluorogentic reporters, electrchemiluminescent tag, and mixtures thereof.

3. The method of claim 2, wherein the reporter enzymes comprises HRP, AP or glucose oxidase and wherein the fluorogentic reporters comprise phycoereythrin.

4. The method of claim 2, wherein the labeling substance is directly conjugated with the primary antibody or indirectly conjugated with a secondary antibody against the primary antibody.

5. The method of claim 4, wherein the primary antibody, the secondary antibody, or both, are pre-labelled with the labelling substance.

6. The method of claim 1, wherein the signals emitted by the immunocomplexes are photons or radiations.

7. The method of claim 1, wherein the signal emitted by the immunocomplexes in each of the plurality of the membrane units is acquired as a numeric value that corresponds to an intensity of the signal.

8. The method of claim 7, wherein the intensity of the signal is not converted from an image.

9. The method of claim 1, wherein the plurality of supports are attached to a planar structure and spaced away from a planar surface of the planar structure.

10. The method of claim 9, wherein the plurality of supports are attached to the planar structure via a linking member, wherein the linking member comprises a first end and a second end, and the first end is attached to the planar structure and one of the plurality of the supports is attached to the linking member at the second end or at a location between the first end and the second end.

11. The method of claim 1, further comprising washing the plurality of membrane units simultaneously in one or more buffer solutions.

12. The method of claim 11, comprising filling the one or more buffer solutions in a plurality of wells in a multi-well plate, and immersing each of the plurality of membrane units in the buffer solution in one of the plurality of wells in the multi-well plate.

13. The method of claim 1, comprising filling a buffer solution in one container, and immersing the plurality of membrane units in the buffer solution in the container.

14. The method of claim 1, wherein the membrane unit is a piece of nitrocellulose or PVDF or a coating of nitrocelluslose or PVDF on a surface.

15. The method of claim 6, wherein the photons are produced by a colorimetric reaction of the labelling substance, a chemiluminesent reaction of the labelling substance, or a fluorescent emission from the labelling substance.

16. A method for immunoblot analysis, comprising:
   providing a multi-unit plate comprising a plurality of membrane units spaced away from one another, wherein:
      each of the plurality of membrane units is individually compartmentalized to
      ensure signal emitted therefrom to be individually acquired, and
      each membrane unit comprises a membrane;
   binding an antigen to one or more of the plurality of membrane units;
   selecting a primary antibody that interacts with the antigen;
   binding the primary antibody to the antigen to form immunocomplexes affixed to one or more of the plurality of membrane units, wherein the primary antibody is directly conjugated with a reporter enzyme, or indirectly conjugated with a reporter enzyme through one or more secondary antibody; and
   detecting from one or more of the membrane units light signals emitted by the reporter enzyme in the immunocomplexes.

17. The method of claim 16, further comprising acquiring light signal emitted from each of the one or more of the membrane units to a numeric value that corresponds to an intensity of the light signal.

18. The method of claim 17, wherein the intensity of the light signals is not measured based on an image of the light signals.

19. The method of claim 16, wherein the membrane unit is a sheet of nitrocellulose or PVDF film or a coating of nitrocelluslose or PVDF on a substrate.

* * * * *

UNITED STATES PATENT AND TRADEMARK OFFICE
CERTIFICATE OF CORRECTION

PATENT NO. : 10,295,544 B2
APPLICATION NO. : 15/433586
DATED : May 21, 2019
INVENTOR(S) : Jiandi Zhang Page 1 of 1

It is certified that error appears in the above-identified patent and that said Letters Patent is hereby corrected as shown below:

On the Title Page

Item (54), and in the Specification, the title of the patent is shown as "APPARATUS AND METHOD FOR HIGH TRHOUGHPUT IMMUNOBLOTING", the correct title is "APPARATUS AND METHOD FOR HIGH THROUGHPUT IMMUNOBLOTING".

Signed and Sealed this
Third Day of September, 2019

Andrei Iancu
*Director of the United States Patent and Trademark Office*